United States Patent

Ohtsuki et al.

[11] Patent Number: 5,947,903
[45] Date of Patent: Sep. 7, 1999

[54] METHOD TO ESTIMATE PLANAR FLOW FROM DOPPLER VELOCITY DISTRIBUTION IN AN OBSERVATION PLANE

[76] Inventors: Shigeo Ohtsuki, 12-15, Yokoyama 2-chome, Sagamihara-shi, Kanagawa, Japan; Motonao Tanaka, 4-26, Kunimi 4-chome, Aoba-ku, Sendai-shi, Miyagi, Japan

[21] Appl. No.: 09/110,146

[22] Filed: Jul. 6, 1998

[30] Foreign Application Priority Data

Jul. 7, 1997 [JP] Japan .................................. 9-181515
Jun. 29, 1998 [JP] Japan ................................ 10-182089

[51] Int. Cl.⁶ ............................................... A61B 8/06
[52] U.S. Cl. ............................................ 600/455; 73/861.25
[58] Field of Search ................................ 600/454–456; 73/861.25–861.27; 367/90

[56] References Cited

U.S. PATENT DOCUMENTS

| | | | |
|---|---|---|---|
| 3,906,791 | 9/1975 | Lynnworth | 73/861.29 |
| 5,010,528 | 4/1991 | Ohtsuki et al. | 600/455 |
| 5,201,313 | 4/1993 | Katkura | 600/455 |
| 5,390,548 | 2/1995 | Kasper et al. | 73/861.15 |
| 5,425,365 | 6/1995 | Iinuma | 600/455 |
| 5,505,204 | 4/1996 | Picot et al. | 600/456 |

FOREIGN PATENT DOCUMENTS 0 379 593 A1  2/1990  European Pat. Off. .

*Primary Examiner*—Francis J. Jaworski
*Attorney, Agent, or Firm*—Dickstein Shapiro Morin & Oshinsky LLP

[57] ABSTRACT

A method for estimating a flow in an observation plane from the Doppler velocity distribution in the observation plane. A Doppler flow function is found from the Doppler velocity distribution by linear integration. A flow rate passing through a path perpendicular to a beam direction is found from the Doppler velocity distribution, and a Doppler flow range function representing a variation of this flow rate in the beam direction is calculated. The Doppler flow range function is separated into a linear boundary flow range function which is a two-dimensional component and a planar boundary flow range function which is a three-dimensional component. The planar boundary flow range function is approximated by a stepwise quantized planar boundary flow range function which varies in unit flow rate, and sink points and source points (simple sources) are determined based on a step position of this quantized planar boundary flow range function. A simple source flow function representing a three-dimensional inflow/outflow to and from the observation plane is calculated from a distribution of simple sources. A smoothed simple source flow function is subtracted from the Doppler flow function so as to calculate a planar flow function. The planar flow function and simple source flow function are combined so as to estimate a planar flow based on a contour line of this combined function.

7 Claims, 13 Drawing Sheets

PLANAR STREAM LINE

METHOD TO ESTIMATE PLANAR FLOW FROM DOPPLER VELOCITY DISTRIBUTION IN AN OBSERVATION PLANE

BACKGROUND OF THE INVENTION

1. Field of the Invention

This invention relates to a method of estimating planar flow from Doppler velocity distribution in an observation plane of a fluid, and more specifically relates to an improved planar flow estimation method that can display a flow velocity distribution as streamlines while utilizing a flow function by estimating an inflow/outflow flow rate of a boundary line or boundary surface.

2. Description of the Prior Art

A method to observe the flow velocity distribution of a fluid in an observation plane by using the Doppler effect of an ultrasonic wave is put to practical use, for example, in observing the rate of blood flow in the heart. Such a blood flow distribution is displayed in color on an ultrasonic wave tomogram of the heart, and is widely used in diagnosing bloodstream in the heart.

This Doppler velocity may be found using electromagnetic waves instead of ultrasonic waves. In recent years, it has been widely used to perform flow velocity observations in oceans, lakes or of cloud movements in the air.

Usually, a Doppler velocity distribution can measure only speed components in the transmitted and received wave directions of the observation beam, however it is necessary to estimate also the component in the direction perpendicular to the beam.

It was thought that the component in the orthogonal direction could be estimated by applying the concept of a stream function, but as blood flow in the heart and current or cloud flows are three dimensional, the estimation was not always satisfactory. Conventionally, surfaces that could be observed with beams are two-dimensional surfaces, this two-dimensional observation plane being obtained by linear or sector scanning with an ultrasonic wave beam or the like. However in a real fluid, there is inflow/outflow to and from the boundary line which is the side boundary of this two-dimensional observation plane. Similarly, there is also inflow/outflow to and from the boundary surface which is a boundary between the observed two-dimensional observation plane and the adjacent (three-dimensional) layer.

Therefore, using conventional methods which take no account of inflow/outflow of fluids on boundary surfaces, there was a problem in that observation and estimation of planar flow in real fluids could not be made.

SUMMARY OF THE INVENTION

This invention, which was conceived in view of the aforesaid current problems, therefore aims to provide an improved estimation method for estimating planar flow which takes account of inflow/outflow to and from a boundary line or boundary plane from only the observed Doppler velocity distribution.

In order to achieve the aforesaid object, this invention comprises a step for scanning an observing beam and scanning a predetermined observation plane in a fluid with this beam, and measuring the Doppler velocity distribution of the fluid from the Doppler frequency of the wave reflected from the observation plane, a step for linearly integrating the Doppler velocity along orthogonal paths which are perpendicular to the beam direction in order to calculate a Doppler flow function at various points on the orthogonal paths, a step for calculating flow rates along these orthogonal paths from the Doppler velocity distribution and calculating a Doppler flow range function representing a variation of this flow rate along the beam direction, a step for separating this Doppler flow range function into a linear boundary flow range function and a planar boundary flow range function based on boundary conditions, a step for quantizing a planar boundary flow function for a predetermined flow rate (referred to as "unit flow rate") and calculating the quantized planar boundary flow rate which varies in a stepwise manner, a step for estimating sink/source points on orthogonal paths corresponding to step positions of the quantized planar boundary flow range function based on the variation rate of the Doppler velocity, a step for calculating a simple source flow function representing flow rates at points in the observation plane due to the effect of the sink/source points from the distribution of sink/source points, a step for calculating a smoothed simple source flow function from this simple source flow function, a step for subtracting this smoothed simple source flow function from the Doppler flow function in order to calculate a Doppler scan planar flow function, a step for calculating a planar flow function by adjusting this Doppler scan planar flow function based on boundary conditions, a step for calculating a quantized flow function by combining this planar flow function and the simple source flow function, and a step for calculating a contour line of this quantized flow function.

DESCRIPTION OF THE PREFERRED EMBODIMENTS

Preferred embodiments of this invention will now be described referring to the attached drawings.

First, in order to describe the principle of this invention, a flow function which is a stream function expanded taking account of flow rate, and the form of its representation, will be described.

A stream function applied to two-dimensional flow represents a flow rate between points. A contour line of this stream function represents a streamline. The direction of a flow velocity vector is known from the tangential direction of the streamline, and the magnitude of the flow velocity is known from a streamline interval. When a planar flow is represented by such a streamline, the whole flow can easily be treated quantitatively. Herein, a stream function and the equivalent expression are shown.

However, a fluid source or sink appears in a two-dimensional observation plane set in a three-dimensional flow, so the flow in the observation plane cannot be considered to be two-dimensional. In this invention, a stream function is expanded so that the flow can be simulated by a streamline representation even in a two-dimensional observation plane in a three-dimensional space. This streamline represents the flow from source to sink. A stream function expanded in this way is called a flow function.

Doppler Velocity and Doppler Flow Rate

Figure 1:
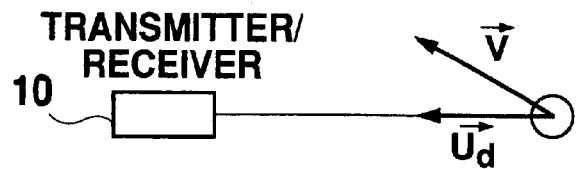
FIG. 1 is a figure for describing the principle of Doppler velocity measurement.

When an observation wave such as an ultrasonic wave is transmitted by a transmitter/receiver, the observation wave is reflected by an object on the beam, and this reflected wave is detected by the transmitter/receiver. In general, a Doppler effect is produced by the reflected wave from the object due to a time variation of a distance r between the transmitter/receiver and the object. Therefore, when the velocity of the object based on a transmitter/receiver 10 is $\vec{V}$ as shown in FIG. 1, only the velocity component $\vec{u}_d$ in the direction of the transmitter/receiver is observed as a frequency variation $f_d$ of the received signal relative to a frequency $f_0$ of the transmitted signal. This frequency variation $f_d$ is called the Doppler frequency, and it increases when the distance r is nearer (i.e., when the reflecting object approaches the transmitter/receiver). The velocity component $\vec{u}_d$ is called the Doppler velocity, and if the propagation velocity of the observation wave is c, the magnitude $u_d$ of the Doppler velocity is expressed as follows:

$$u_d = c \frac{f_d}{2f_0} \quad [1]$$

Figure 2:
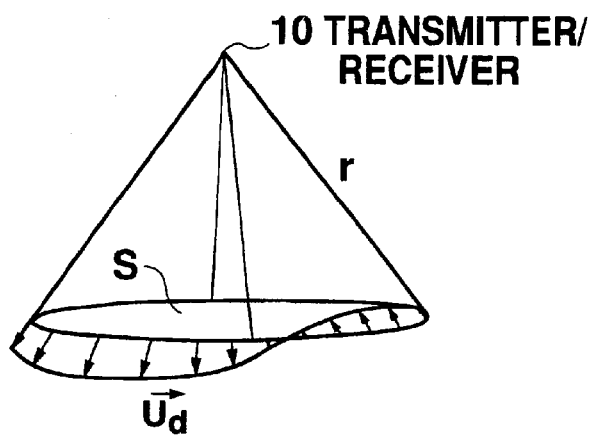
FIG. 2 is a schematic diagram showing a relation between Doppler velocity and Doppler flow rate taking a three-dimensional observed object as an example.
Figure 3:
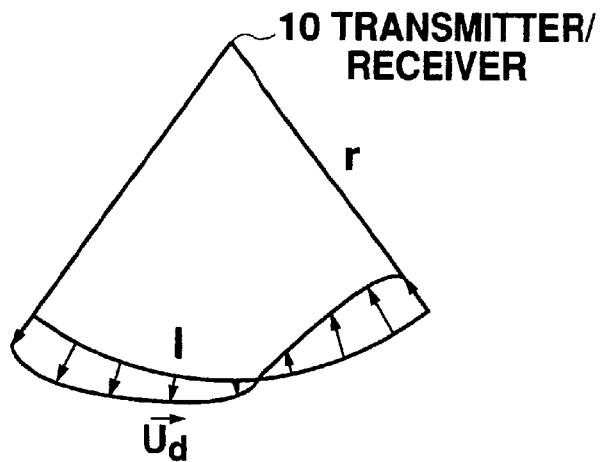
FIG. 3 is a schematic diagram showing a two-dimensional relation between Doppler velocity and Doppler flow rate

However, when the distance r is fixed as seen from the transmitter/receiver, the observation area is a plane S in the three-dimensional case, as shown in FIG. 2. As the Doppler velocity $u_d$ is the normal direction to the plane S, the amount of fluid, i.e. the flow rate $Q_d(r)$ passing through this surface can be found by integrating the magnitude $u_d$ of the Doppler velocity on the plane S:

$$Q_d(r) = \int_S u_d(r) dS \quad [2]$$

This quantity will be referred to as a (three-dimensional) Doppler flow rate.

When the observation area is two-dimensional, the distance r is a line l when it is fixed, so the (two-dimensional) Doppler flow rate $Q_d(r)$ is given by the following expression:

$$Q_d(r) = \int_l u_d(r) dl \quad [3]$$

In the three-dimensional space of Cartesian coordinates when the direction of the observation wave beam is the x direction, the observation plane is set in the x-y plane relative to a given $z_0$ (i.e., the plane where $z=z_0$). The Doppler velocity $u_d(x,y,z_0)$ which is then observed has the opposite sign to the velocity component $u(x,y,z_0)$ of the observed fluid. In other words, $$u_d = -u \quad [4]$$

Herein, the velocity component $u_d(x,y,z_0)$ is linearly integrated from $y_0$ to $y1$, which is the observation range in the y direction, with x as a parameter. This is the Doppler flow rate $Q_d(x)$ in an interval $[y_0, y_1]$ when x is fixed in the x-y plane. In other words, $$Q_d(x) = \int_{y_0}^{y_1} u_d(x,y) dy = -\int_{y_0}^{y_1} u(x,y) dy \quad [5]$$

Equation of Continuity, a Basic Property of the Fluid

For a flow with a velocity vector $\vec{V}(t, \vec{r})$ at a time t and position $\vec{r}$, when the mass of the fluid is conserved, the following equation of continuity holds where the density is ρ:

$$\text{div}(\rho \vec{V}) = 0 \quad [6]$$

If the fluid is assumed to be incompressible, the equation of continuity is as follows as the density ρ is fixed:

$$\text{div}(\vec{V}) = 0 \quad [7]$$

If this is expressed in rectangular coordinates x, y, z, the velocity components u, v, w are respectively given as follows:

$$\frac{\partial u}{\partial x} + \frac{\partial v}{\partial y} + \frac{\partial \omega}{\partial z} = 0 \qquad [8]$$

Two Dimensional Flow of Incompressible Fluid

For two-dimensional flow of an incompressible fluid, the main points of the stream function applied to two-dimensional flow will be shown before expanding the stream function.

Consider a two-dimensional flow of the incompressible fluid in the x-y plane where there is no flow in the z direction. Representing the velocity components in the x, y directions respectively as u, v, a stream function S(x, y) is defined as follows:

$$\frac{\partial S}{\partial y} = u \qquad [9]$$

$$\frac{\partial S}{\partial x} = -v \qquad [10]$$

From this relation, the following equation is obtained.

$$\frac{\partial u}{\partial x} + \frac{\partial v}{\partial y} = \frac{\partial}{\partial x}\left(\frac{\partial S}{\partial y}\right) + \frac{\partial}{\partial y}\left(-\frac{\partial S}{\partial x}\right) = \frac{\partial^2 S}{\partial x \partial y} - \frac{\partial^2 S}{\partial x \partial y} = 0 \qquad [11]$$

Hence, a two-dimensional equation of continuity is satisfied, and it also means that the a stream function thus defined cannot be applied to general three-dimensional flow.

It is well known that when two points are selected in the two-dimensional incompressible flow and the flow rate across the path joining them is considered, the flow rate is constant when the equation of continuity is satisfied, and the value of the flow rate at that time is equal to the difference in the values of the stream function at these two points.

In other words, the stream function can be adapted to this flow rate, and the stream function for two-dimensional flow represents a flow rate based on one point.

Next, it will be shown that the contour line of the stream function is a streamline.

Suppose the value of a stream function S(x,y) is constant (Const). The following equation may then be written:

$$S(x,y) = \text{Const} \qquad [12]$$

When this is differentiated, the following is obtained:

$$dS(x, y) = \frac{\partial S}{\partial x}dx + \frac{\partial S}{\partial y}dy = -vdx + udy = 0 \qquad [13]$$

i.e., $$\frac{dy}{dx} = \frac{v}{u} \qquad [14]$$

From this equation, it is seen that the tangential direction of the contour line coincides with the direction of the flow velocity vector. In other words, the contour line of the stream function is a streamline of a two-dimensional flow.

Streamline and Flow Function of Observation Plane in Three-dimensional Flow

Consider that a field of three-dimensional flow velocity vectors $\vec{V}(x,y,z)$ is observed in the x-y plane, and that information is obtained for a field of two-dimensional flow velocity vector components $\vec{U}(x,y)$. Assume that the ultrasonic wave beam is emitted in the x direction, and, due to the Doppler effect, the flow velocity vector component in the x direction is observed as the Doppler velocity $u_d$. Assume further that scanning is performed with this observation wave beam in the y direction, and that the distribution of the Doppler velocity $u_d$ in the observation plane is observed. Now, under such a limitation, let us calculate a flow function which is an expanded stream function so that the streamline in the observation plane can be drawn in three-dimensional flow.

Figure 4:
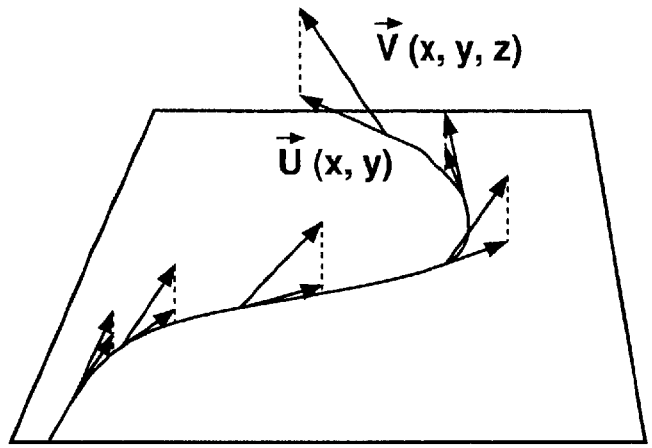
FIG. 4 is a schematic diagram of a planar streamline.

Planar Flow Velocity Distribution and Planar Streamline Representing this Information Here, we will consider streamline in order to better understand the characteristics of the planar distribution of the flow velocity vector component $\vec{U}(x,y)$ in a two-dimensional plane. As in the case of streamline in a flow velocity field in three-dimensional space, the streamline in the observation plane is defined as follows. When the direction of the tangent of a curve coincides with the direction of the flow velocity vector component $\vec{U}$ as shown in FIG. 4, this curve is referred to as a planar streamline. The characteristics of the flow in the observation plane are represented by this planar streamline.

Flow Function as an Expansion of Stream Function

In general, in an observation plane in three-dimensional flow, there is a three-dimensional inflow/outflow. Let us expand the stream function so that it can also be applied to this case, and let us focus our attention on the following two characteristics of the streamline defined in two-dimensional flow.

(1) The contour line of the stream function is a streamline.

(2) Flow rate can be expressed quantitatively by fixing the flow rate between streamlines.

To apply feature (2) of the stream function also in the case where there is an inflow/outflow to and from the observation plane, the three-dimensional inflow/outflow continually dispersed in the observation plane is quantized in a predetermined unit flowrate q. In other words, according to this embodiment, the three-dimensional inflow/outflow dispersed in the observation plane is approximated by arranging the source and sink of a unit flow rate q to be in the observation plane. This source and sink of unit flow rate q will be referred to as a simple source.

Simple Source Flow Function and Layer Structure

Figure 5:
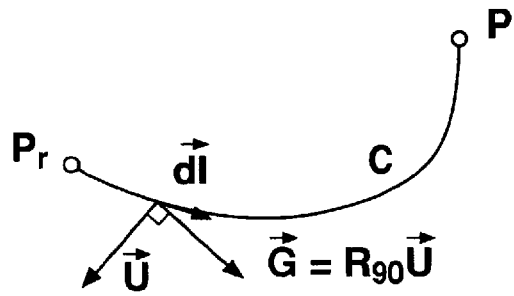
FIG. 5 is a schematic diagram of a definition of flow rate between two points.

Let us calculate a flow rate Q by linear integration along a curve C in the x-y plane as shown in FIG. 5. To express the flowrate by the inner product of vectors, an operator which rotates the vector by 90° in a plane is written as $R_{90}$, and a vector $\vec{G}(x,y)$ obtained by rotating the flow velocity vector planar component $\vec{U}(x,y)$ by 90° is considered as a flow gradient vector. This flow gradient vector $\vec{G}(x,y)$ may be expressed as follows:

$$\vec{G}(x,y) = R_{90}\vec{U}(x,y) \qquad [15]$$

As a result, the flow rate Q crossing the curve C between the points $P_r$ and P in FIG. 5 may be found by linear integration as an inner product of vectors as follows:

$$Q = \int_C \vec{G} \cdot \vec{dl} \qquad [16]$$

Herein, the flow function Q(x,y) related to the reference point $P_r$ in FIG. 5 is defined as a flowrate for an arbitrary path C joining the reference point $P_r$ and an arbitrary point $P(x,y)$, i.e.,:

$$Q(x, y) = \int_C \vec{G} \cdot \vec{dl} \quad [17]$$

Figure 6:
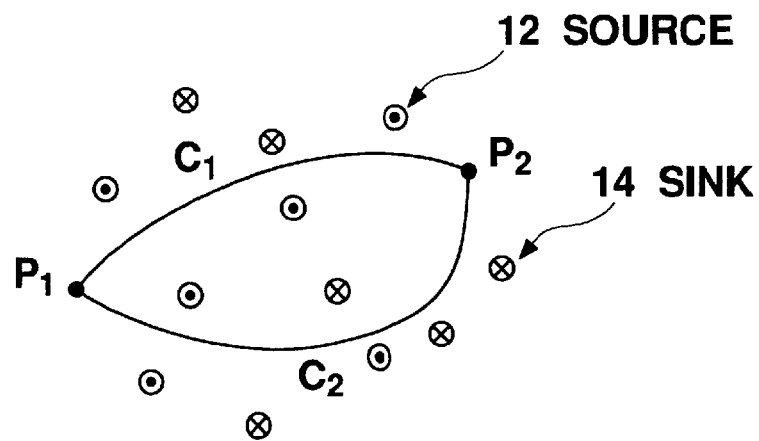
FIG. 6 is a schematic diagram showing a relation of point sources (simple sources) and a flow rate between two points.

Here, consider the relation between a flow rate $Q_1$ for a path with a curve $C_1$ and a flow rate $Q_2$ for a path with a curve $C_2$ when there are two paths $C_1$, $C_2$ from a point $P_1$ to a point $P_2$ in FIG. 6.

If there are $n_p$ sources 12 for unit flow rate q and $n_k$ sinks for unit flow rate q in an area enclosed by these two curves, $$Q_1 = Q_2 + n_p q - n_k q = Q_2 + nq \quad [18]$$

The value of n depends on the path.

If the stream function is generalized as representing flow rate, and this is defined as the flow function, the flow function $Q(x, y)$ of a point $P(x,y)$ in the observation plane may be defined as a multi-valued function which has a discrete value for unit flow rate q based on a given value. The fluid which gives rise to the flow rate in the observation area represented by this flow function $Q(x,y)$, is supplied from simple sources (i.e., source, sink) in the observation plane and the boundary line of the observation area.

Hence, the flow function $Q(x,y)$ may be split into a simple source flow function $Q_p(x,y)$ which is a multi-valued function representing a flow rate due to the source and sink point sources (simple sources), and a linear boundary flow function $Q_b(x,y)$ of a single-valued function considering only inflow/outflow to and from the boundary line, i.e., $$Q(x,y) = Q_b(x,y) + Q_p(x,y) \quad [19]$$

Herein, the linear boundary flow function is a stream function for two-dimensional flow.

As a result, by using a flow function which is an expanded stream function, the characteristic (1) of stream functions in two-dimensional flow can be applied even to a plane with inflow/outflow. The flow function of the point source (simple source) can then be illustrated as shown in FIG. 7 and FIG. 8.

Figure 7:
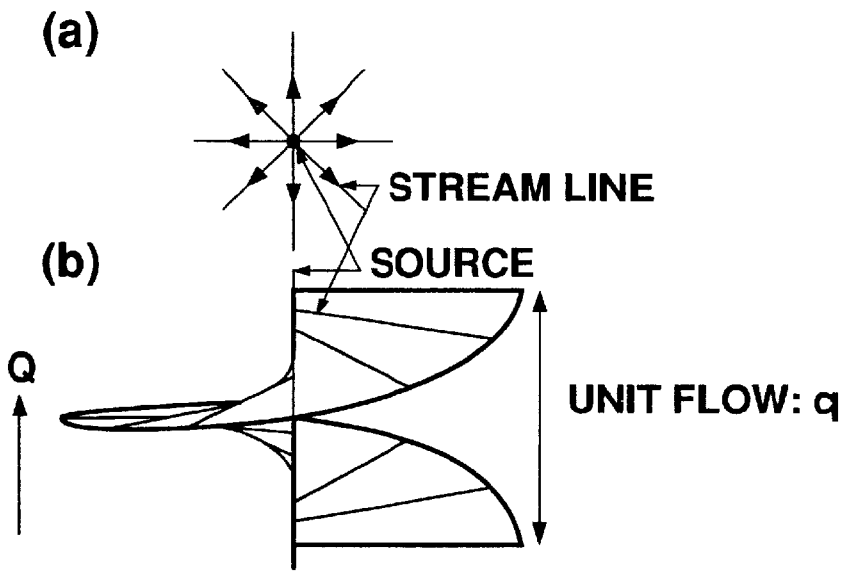
FIG. 7 is a schematic diagram of a point source (streamline starting point) and a spiral slope representing a simple source flow function in the case of a source.

FIG. 7 is a figure for describing a flow function of a source (streamline starting point). As shown in (a), at the position of the source point, the flow rate varies by the unit flow q. On a clockwise path the flow rate increases, and on an anticlockwise path the flow rate decreases. The flow rate is different even at the same end point for paths containing the point source, and this difference is the unit flow q.

Hence, the flow rate is multi-valued in a plane comprising the source point. Taking the flow rate as height, the flow rate around the source point has a layer structure with a spiral slope which continues infinitely upwards and downwards as shown in (b). The flow function of the slope structure at this point source is taken as the simple source flow function $Q_p(x,y)$.

Figure 8:
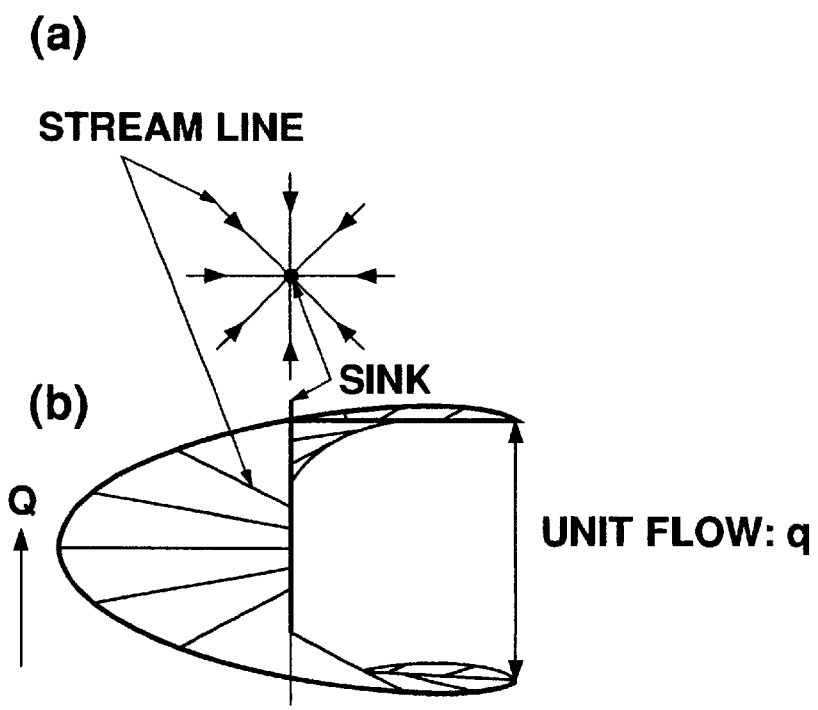
FIG. 8 is a schematic diagram of a point source (streamline end point) and a spiral slope representing a simple source flow function in the case of a sink.

FIG. 8 is a figure for describing a flow function of a sink point source. This case may be treated in a similar manner to that of the source described hereabove. Specifically, (a) the flow rate decreases on a clockwise path around the sink point source, and the flow rate increases on an anticlockwise path around the sink point. Therefore, the flow rate around the sink point has a layer structure with a spiral slope which continues infinitely upwards and downwards as shown in (b). This is also the simple source flow function $Q_p(x,y)$.

It should be noted that when there is no point source (simple source) in the observation plane, the simple source flow function $Q_p(x,y)$ is zero.

Flow Function and Streamline

As described hereabove, by concentrating a continuously dispersed inflow/outflow for unit flow rate and treating it as a point source (simple source), a general flow in an observation plane comprising a three-dimensional inflow/outflow may be expressed as a discrete flow function.

As this discrete flow function varies at unit flow rate intervals for each layer, the contour lines for unit flow rate coincide for all layers. These contour lines can therefore be grouped together and represented as a streamline in the observation plane.

In other words, the streamlines of the unit flow rate interval can be expressed by contour lines which coincide for all layers of the discrete flow function. Hereafter, the discrete flow function will be referred to simply as flow function.

Scan Flow Function, a Single-valued Function Expressing the Flow Function

Flow functions which can represent point sources (simple sources) are generally multi-valued, and this is inconvenient for handling numerical data. As the value of the flow function is a multi-value which takes a discrete value for unit flow rate, we shall therefore consider expressing the flow function as a combination of a unit flow rate and a single-valued function.

If we specify one path from a reference point to a point for which it is desired to calculate the value of a function, we obtain a single-valued function. To obtain this, there is one path from the reference point, a method is specified that can scan the entire observation area and the value of the function is determined for each point.

The single-valued function found in this way will be referred to as a scan flow function. Discontinuities in this scan flow function represent differences of the layers, and continuous flow function values for the same layer may be obtained by adjusting the unit flow rate.

Figure 9:
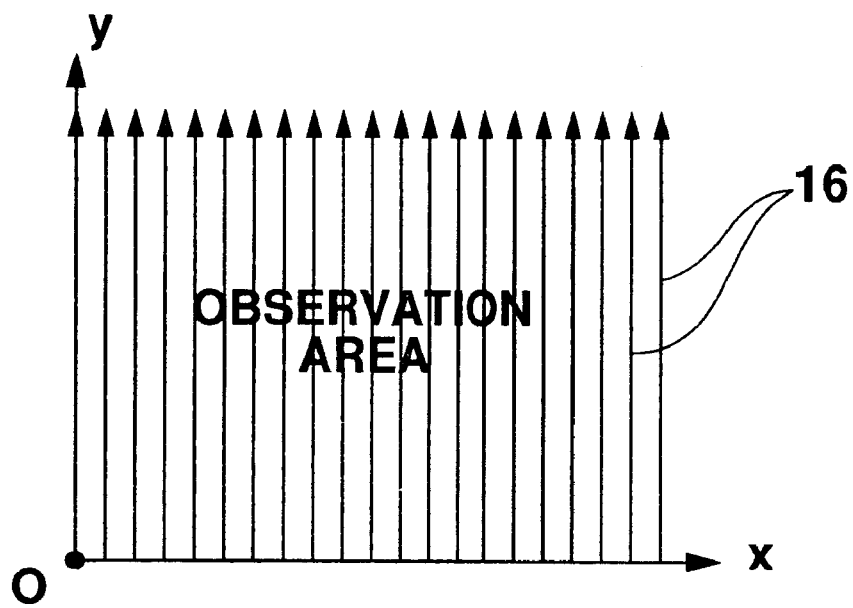
FIG. 9 is a figure showing an example of a path for calculating a flow function by linear scanning.
Figure 10:
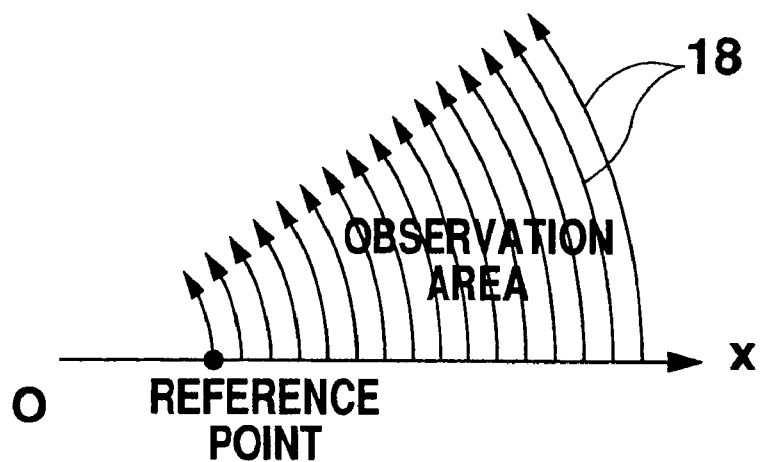
FIG. 10 is a figure showing an example of a path for calculating a flow function by sector scanning.

FIG. 9 shows an example of a path for calculating a linear scan flow function by linear scanning in Cartesian coordinate system, and FIG. 10 shows an example of a path for calculating a sector scan flow function by sector scanning in polar coordinate system.

The integration path for calculating the linear scan flow function is shown by arrowed lines 16 for which x=k (constant) shown in FIG. 9. The integration path for calculating the sector scan flow function is shown by arrowed arcs 18 for which r=k(constant) shown in FIG. 10.

Flow Function Method and Streamline Display

The stream function was expanded so that it could be applied also to the case where there is inflow/outflow to and from the observation plane, and this was taken as a flow function. The method wherein the flow function is calculated from measured Doppler data and a streamline deduced therefrom is displayed superposed on the Doppler image will be referred to as a flow function method. The flow velocity vector component in the observation area can be estimated from the streamline.

In the following description of the flow function method, the case of observing blood flow in the heart will be considered, and polar coordinate system will be used with the position of the ultrasonic wave probe as origin.

Doppler Flow Rate and Quantization of the Inflow/Outflow to and from Plane

Figure 11:
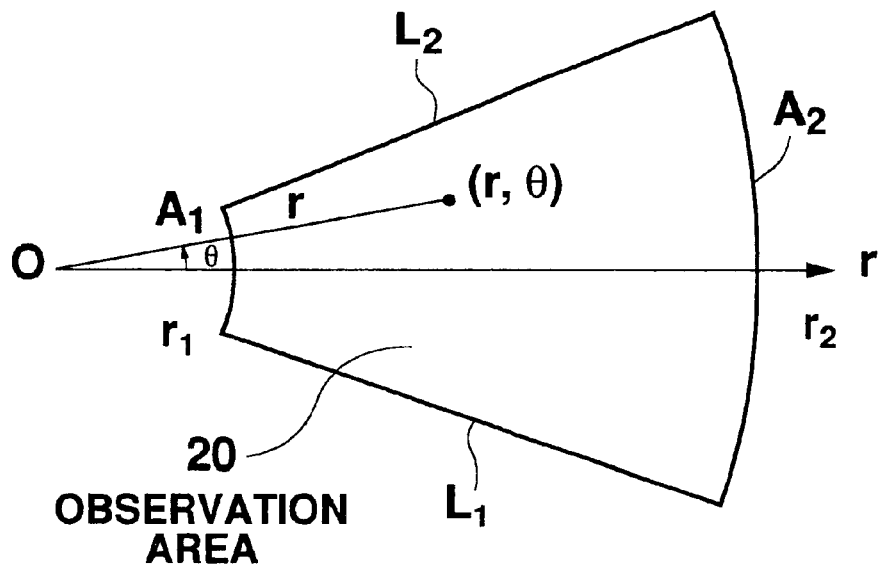
FIG. 11 is a schematic diagram showing a relation between a Doppler velocity observation region and polar coordinates.
Figure 12:
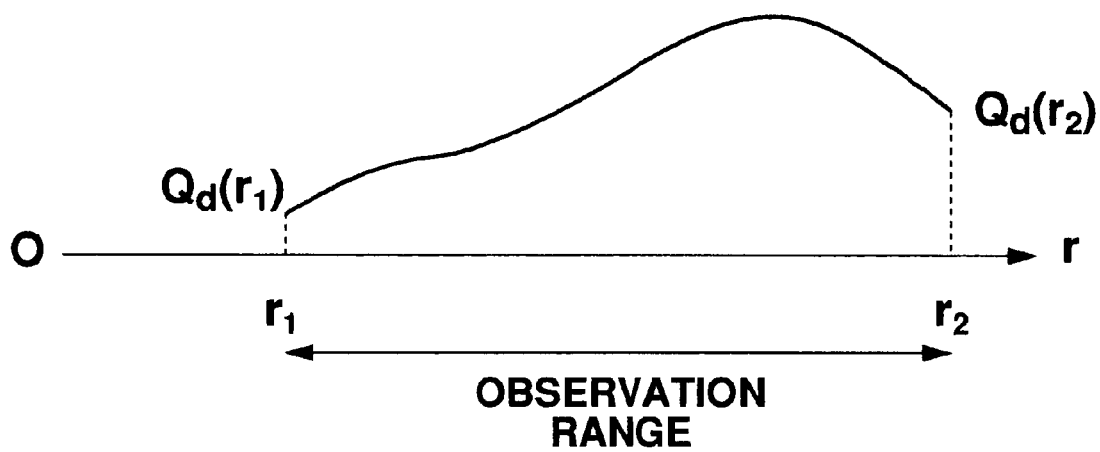
FIG. 12 is a schematic diagram of a Doppler flow range function obtained as a function of beam direction.

First, assume that an observation area 20 in the observation plane is an area having straight line boundaries and arc boundaries as shown in FIG. 11. The Doppler flow range function $Q_d(r)$ shown in FIG. 12 is found from the Doppler velocity distribution in this area. The Doppler flow range function $Q_d(r)$ shows the flow passing through an arc-shaped path at a distance r from an origin O in the observation area. Specifically, the Doppler flow range function is found by linearly integrating the Doppler velocity at each point on the arc from one end of the arc to the other.

A Doppler flow rate $Q_d(r_1)$ represents a flow rate flowing out from an arc boundary $A_1$ (distance $r_1$ from the origin), and a Doppler flow rate $Q_d(r_2)$ represents a flow rate flowing out from an arc boundary $A_2$ (distance $r_2$ from the origin). The variation of the Doppler flow range function $Q_d(r)$ from $r_1$ to $r_2$ represents the inflow/outflow to and from the observation area from the side boundaries $L_1$, $L_2$ and from outside the plane.

Figure 13:
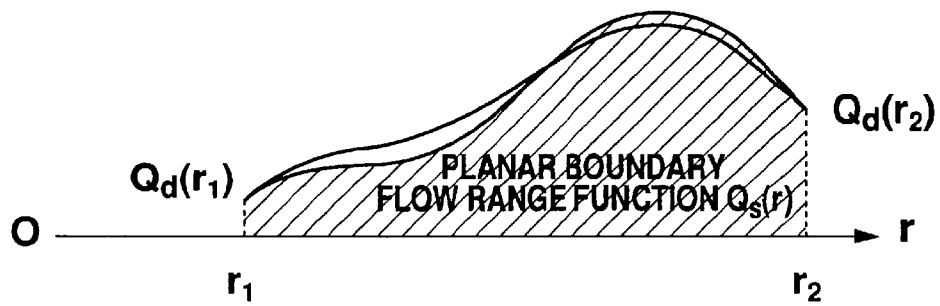
FIG. 13 is a schematic diagram showing a state where a planar boundary flow range function has been separated from the Doppler flow range function.

The flow rate due to inflow/outflow to and from the side boundaries $L_1$, $L_2$ of the observation area is expressed by a linear boundary flow range function $Q_b(r)$. The linear boundary flow range function $Q_b(r)$ can be found from the boundary conditions of the observation area. The flow rate remaining after subtracting the linear boundary flow range function $Q_b(r)$ from the Doppler flow range function $Q_d(r)$ will be referred to as a planar boundary flow range function $Q_s(r)$ (FIG. 13). The planar boundary flow range function represents the three-dimensional inflow/outflow to and from the arc boundaries A1, A2 and from outside the plane.

Figure 14:
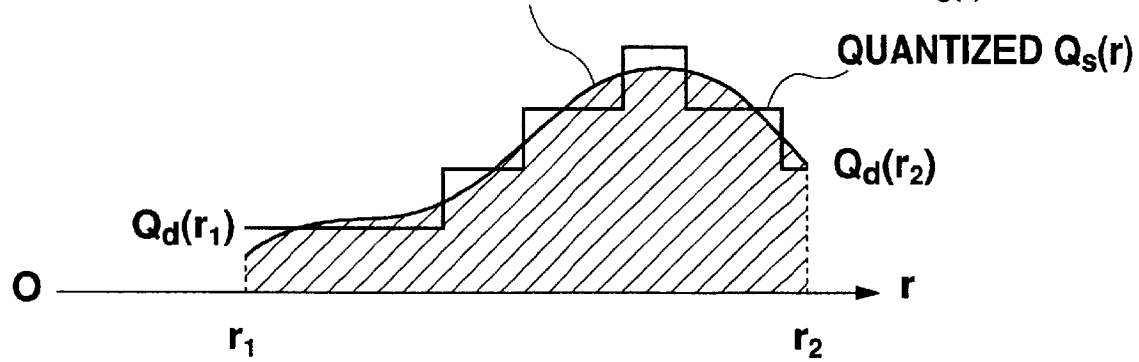
FIG. 14 is a schematic diagram describing the principle of quantizing the planar boundary flow range function.

Next, this planar boundary flow range function $Q_s(r)$ is quantized (FIG. 14). If the unit flow rate of quantization is q, a quantized planar boundary flow range function $Q_{qs}(r)$ is approximated by the stepwise graph of FIG. 14. The step of this stepwise graph corresponds to a point source (simple source). A descending step is a source (streamline starting point), and an ascending step is a sink (streamline finishing point).

Estimation of Position of Point Source (Streamline) and Simple Source Flow Function From the above procedure, the type of simple source (streamline starting point, streamline end point) representing source/sink for the observation area and the distance of each simple source from the origin is found.

Next, the position of each simple source on the arc is estimated. There should be a large rate of variation in the range of Doppler velocity in the vicinity of a simple source (source or sink). Therefore, when the simple source is a source, the position on the arc where the variation rate of beam direction of Doppler velocity is negative and its magnitude is a maximum, is estimated as the position of the simple source. On the other hand when the simple source is a sink, the position where the variation rate of beam direction of Doppler velocity is a positive maximum is estimated as the position of the simple source.

Figure 15:
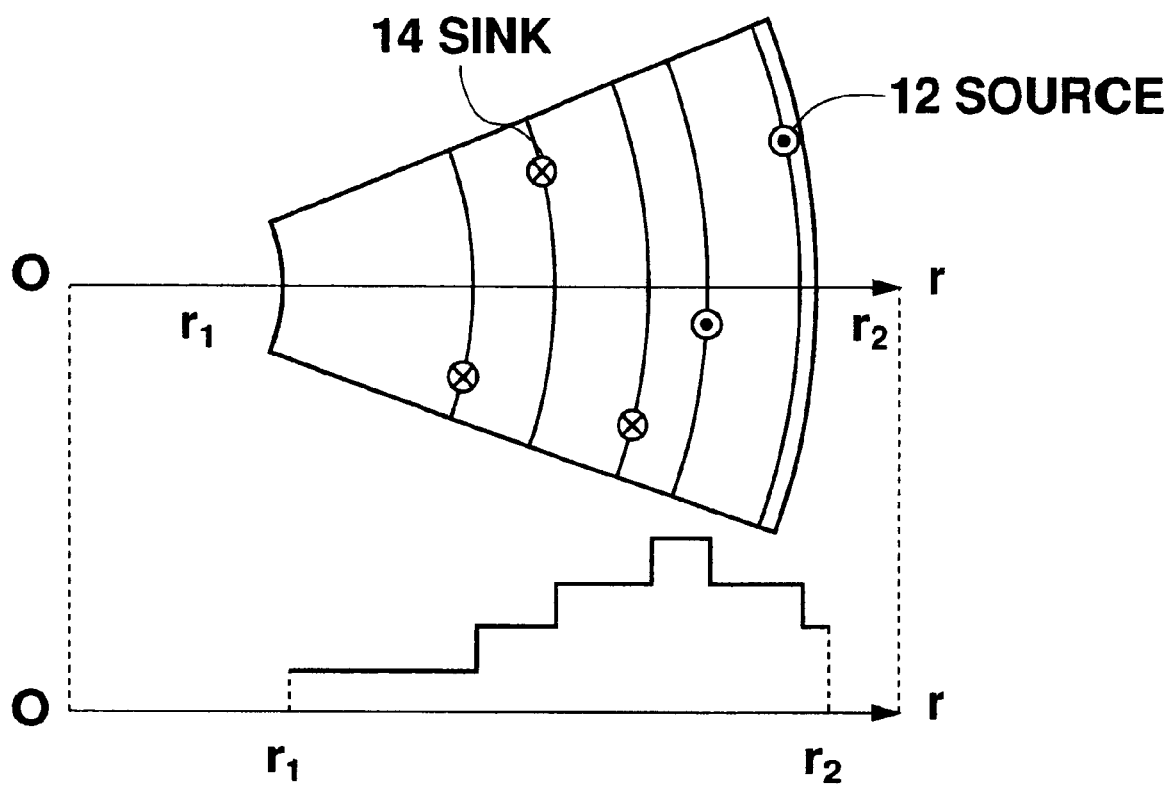
FIG. 15 is a schematic diagram showing a relation between the quantized planar boundary flow range function and point sources (simple sources).

In this way, the positions of point sources (simple sources) in the observation area can be estimated (FIG. 15).

A simple source flow function can be determined for each of the simple sources found in this way taking account of the spiral slope structure. Also, the superposition of all the simple source flow functions of these simple sources is the simple source flow function $Q_{qs}(r,\theta)$ of the observation area.

Doppler Flow Function and Corresponding Simple Source Flow Function

Next, the Doppler flow function $Q_d(r, \theta)$ will be defined. In the sector-shaped observation area where the ultrasonic wave probe is at the origin point O, one side boundary line is taken as a reference line. Then, considering an arc (distance r from starting point) when the Doppler flow range function $Q_d(r)$ is calculated, a point both on this arc and the reference line is taken as a reference point. The integration result when the Doppler velocity is integrated from the reference point to an arbitrary point (at an angle θ from the reference line) on the arc, is defined as the Doppler flow function $Q_d(r, \theta)$ at that point (r,θ).

A Doppler scan simple source flow function $Q_{ds}(r,\theta)$ is also found for simple sources by performing the same scan as for the Doppler flow function. Specifically, for a simple source distribution in the observation plane found by the aforesaid method, the Doppler scan simple source flow function $Q_{ds}(r,\theta)$ is found by performing linear integration on the same arc path as when the Doppler flow function is found.

When this Doppler scan simple source flow function is used, the simple source flow function which is a multi-valued function can be displayed as a single-valued function. In other words, with the Doppler scan simple source flow function, the integration path (scanning path) is uniquely determined, so that the value of the function at each point is also uniquely determined. In a polar coordinate display, the simple source flow function $Q_s(r,\theta)$ is expressed by the Doppler scan simple source flow function $Q_{ds}(r, \theta)$, the one side linear boundary flow function $Q_{bo}(r)$ and the unit flow rate q as follows:

$$Q_{qs}(r,\theta)=Q_{ds}(r,\theta)+Q_{bo}(r)+nq \quad [20]$$

where n is an arbitrary integer.

The one side linear boundary flow function $Q_{bo}(r)$ represents the flow rate on the side of the boundary line of the observation area which was taken as a reference line to calculate the Doppler flow function $Q_d(r,\theta)$. The one side linear boundary flow function $Q_d(r,\theta)$ which is a function of the distance from the starting point, can be estimated from a real-time tomogram of the observation area obtained by transmission and reception of the observation wave beam.

Two-dimensional Display by Quantized Flow Function

The Doppler flow function $Q_d(r,\theta)$ can be computed based on the observed Doppler velocity distribution $u_d(r,\theta)$. This may be expressed as the sum of a smoothed simple source flow function $<Q_{qs}(r,\theta)>$ representing planar inflow/outflow, and a Doppler scan planar flow function $Q_{d2}(r, \theta)$ which takes account of inflow/outflow to and from the boundary line as a two-dimensional flow.

$$Q_d(r,\theta)=<Q_{qs}(r,\theta)>+Q_{d2}(r,\theta) \quad [21]$$

A simple source Doppler flow function $Q_{qs}(r,\theta)$ is calculated from the distribution of point sources (sink or source) which is determined by quantizing the inflow/outflow amount of the smoothed simple source flow function $<Q_{qs}(r, \theta)>$ of planar inflow/outflow. Conversely, the smoothed simple source flow function $<Q_{qs}(r,\theta)>$ may be calculated by smoothing the simple source flow function $Q_{qs}(r, \theta)$. The Doppler scan planar flow function $Q_{d2}(r, \theta)$ may then be computed by the following equation:

$$Q_{d2}(r,\theta)=Q_d(r,\theta)-<Q_{qs}(r,\theta)> \quad [22]$$

As will be understood from the way in which it is calculated, the Doppler scan planar flow amount function $Q_{d2}(r,\theta)$ is a value found along an arc passing through a point on a side boundary of the observation area (i.e., the reference line), and if r is different, the reference point when the function is calculated will also be different.

A bias C(r) is introduced in order to standardize the reference points of this function to the origin of the observation area. The bias C(r) represents a flow rate through a path from the origin to a point at a distance r on the reference line. The bias C(r) may be estimated from a realtime tomogram of the observation area obtained by transmission and reception of the observation wave beam. For example, in an ultrasonic wave tomogram of the heart, the bias C(r) may be found based on the displacement of points on the inner wall of the heart between two-frames of tomogram, and the time interval between the two frames. Therefore, the Doppler scan planar flow function $Q_{d2}(r, \theta)$ may be found taking account of the boundary conditions by adjusting the bias C(r) for each distance r. Specifically:

$$Q_2(r,\theta)=Q_{d2}(r,\theta)+C(r) \quad [23]$$

Herein, this bias C(r) may also be adjusted beforehand so as to eliminate quantization error when the planar boundary flow range function is quantized.

As a result, the quantized flow function $Q_q(r,\theta)$ which can display the flow function $Q(r,\theta)$ on a surface, may be written as follows:

$$Q_q(r,\theta)=Q_{qs}(r,\theta)+Q_2(r,\theta) \quad [24]$$

By finding the contour line of this quantized flow function $Q_q(r,\theta)$, a planar streamline in the observation area can be displayed.

Streamline Display Using Quantized Flow Function

The streamline of a two-dimensional flow may be expressed by the contour line of the stream function. Herein, the flow function which can be applied even when there is a three-dimensional inflow/outflow to and from an observation plane with two-dimensional flow, is multi-valued. It can be expressed by a single-valued function by specifying the integration path when the function is found. The data for the function may be treated as two-dimensional data. A layer structure of the flow function is determined as discontinuities in the data.

To draw the streamline, instead of using a flow function directly, it is practical to use two-dimensional data representing a quantized flow function which is calculated by the predetermined estimates the scanning method (i.e., way of using the integration path). Taking account of the layer structure of flow function, a correction value is applied to increase/decrease the unit flow rate q when discontinuities are expected in data values, and a planar streamline which is the contour line of quantized is drawn when the data can be considered to belong to the same layer.

As already mentioned, the flow rate difference between layers is the unit flow rate q, so the contour line of the unit flow rate intervals of all layers is displayed as the same planar streamline.

Therefore, if inflow/outflow to and from the observation plane is approximated by a distribution of simple sources with unit flow rate q, the planar flow may be represented by a (quantized) flow function, and if the contour lines of this (quantized) flow function are drawn with the unit flow rate interval, planar a streamline display is obtained.

Applying this, a flow estimated from planar flow information obtained by Doppler weather radar for observing atmospheric flow, or by medical ultrasonic wave color Doppler devices for observing blood flow in the heart, can be displayed as a streamline.

Embodiment for Linear Scan System

As described hereabove, according to the principle of this invention, a linear boundary flow function and a planar boundary flow function are estimated from a Doppler velocity distribution of a wave reflected from an observation plane, and a planar flow can be estimated based thereon by combining the planar flow function and a simple source flow function. Herebelow, the estimation method of this invention will be described in further detail.

Figure 16:
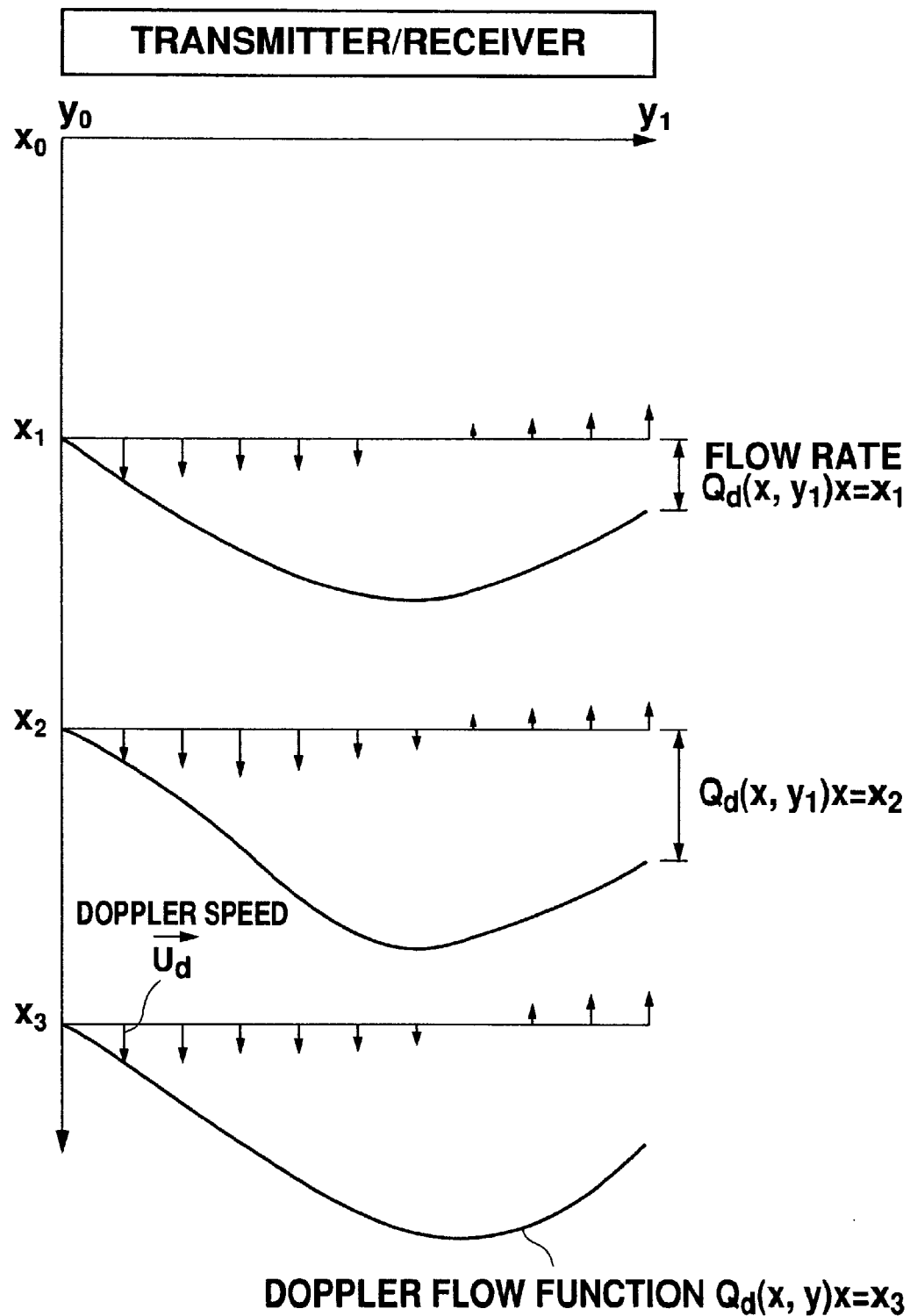
FIG. 16 is a schematic diagram showing an example of a linearly scanned Doppler velocity.

FIG. 16 shows an example of Doppler velocity distribution calculated on the basis of the observation wave beam transmitted from a transmitter/receiver when the x-y plane is the observation plane. In the aforesaid description of the principle of the invention, sector scanning was used as an example, but in the following embodiment, a linear scanning observation wave beam is used.

As is clear from the diagram, the observation wave beam from the transmitter/receiver is transmitted in the x direction, and as a result, only the x direction component of the Doppler velocity $\vec{U}$ is obtained. The linear scanning in the figure is performed relative to the y direction, and an observation plane along the scan axis in the y direction is set from y0–y1. In FIG. 16, only three Doppler velocitys in the x direction, i.e. x1, x2, x3, are shown on the axis in order to simplify the explanation.

First, in the observation plane x-y, a Doppler flow rate in and Doppler flow function are found in an orthogonal direction to the beam direction, i.e., along the y direction. For this purpose, the Doppler velocity is linearly integrated from y0 to y along each of the axes x=x1, x2, x3 perpendicular to the beam direction, and as a result, the Doppler flow function $Q_d(x, y)$ is found.

Also, the Doppler flow range function $Q_d(x)$ at a distance x is found by integrating the Doppler velocity from y0 to y1 along a perpendicular axis to the beam direction at a position at a distance x from the transmitter/receiver.

Figure 17:
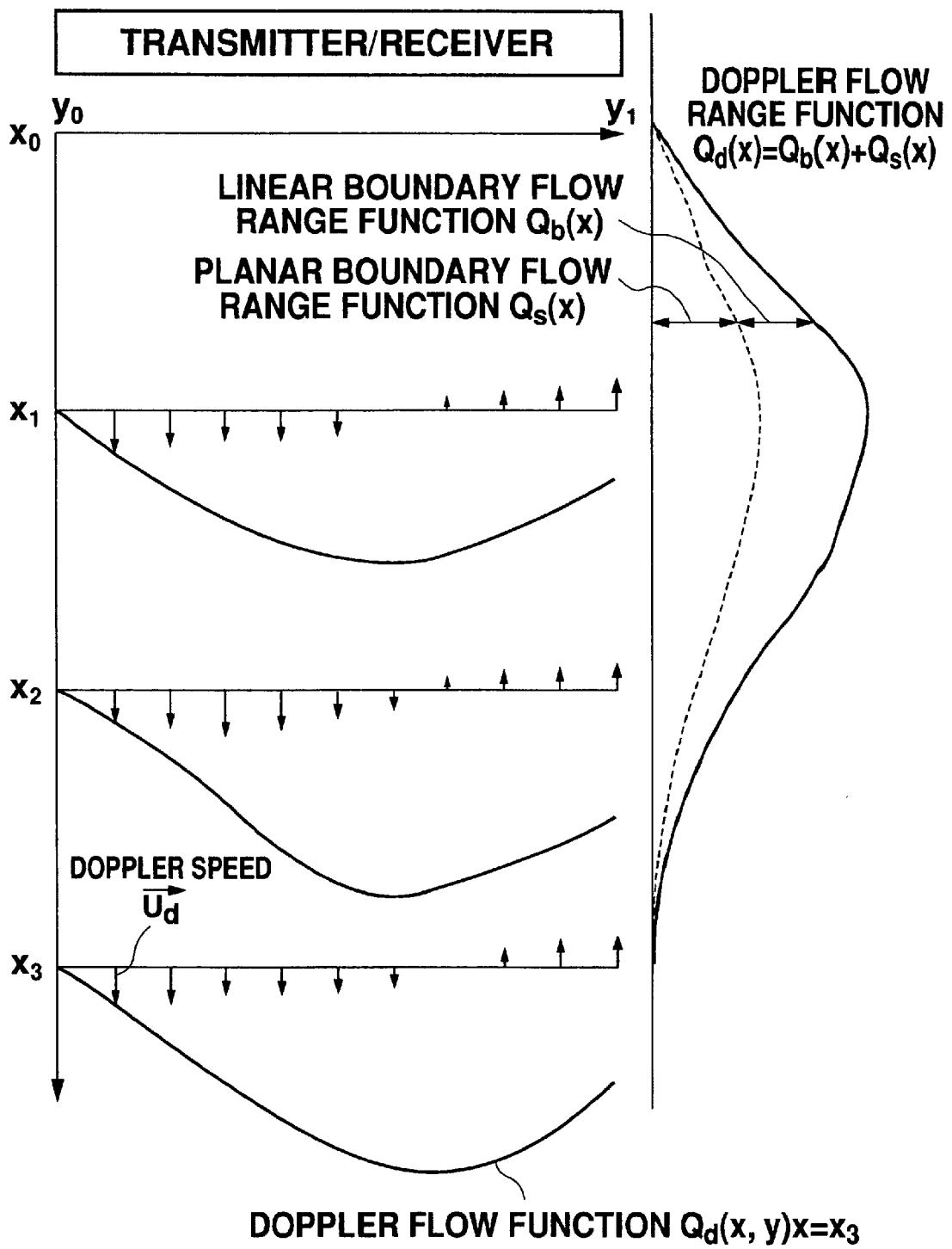
FIG. 17 is a schematic diagram showing a state wherein the Doppler flow range function is split into a two-dimensional planar component and a three-dimensional inflow outflow component.

FIG. 17 shows the Doppler flow rate along the x axis direction, and the Doppler flow range function $Q_d(x)$ is shown by a solid line. This $Q_d(x)$ contains a linear boundary flow range function $Q_b(x)$ representing a two-dimensional inflow/outflow to and from a boundary line of the observation area and a planar boundary flow range function $Q_s(x)$ representing a three-dimensional inflow/outflow to and from the observation area. In other words, the Doppler flow range function found as described hereabove is split into a linear boundary flow range function and planar boundary flow range function based on the boundary condition in the observation area. This boundary condition is very different according to the nature of the observing area, and the linear boundary flow range function $Q_b(x)$ can be determined by a time-dependent displacement of the boundary line of a tomogram. For example, in the ultrasonic wave diagnosis of the heart, the inner wall of the heart is taken as the boundary line, and the linear boundary flow range function $Q_b(x)$ is found from a time-dependent change of the position of the heart inner wall in the real-time diagnosis image. The planar boundary flow range function $Q_s(x)$ can be found as a difference between the Doppler flow range function $Q_d(x)$ and the linear boundary flow range function $Q_b(x)$.

In this way, when the flow rate flowing out or in from a two-dimensional direction, i.e., from a side boundary of the observation plane along the x axis (linear boundary flow range function $Q_b(x)$) and the flow rate flowing out or in between layers in a three-dimensional direction (planar boundary flow range function $Q_s(x)$) are calculated, a planar flow function and a simple source flow function based on them can be found separately.

The simple source flow function denotes sources/sinks in a three-dimensional direction. The simple source flow function $Q_{qs}$ can be found using the planar boundary flow range function $Q_s(x)$ shown by FIG. 17.

Figure 18:
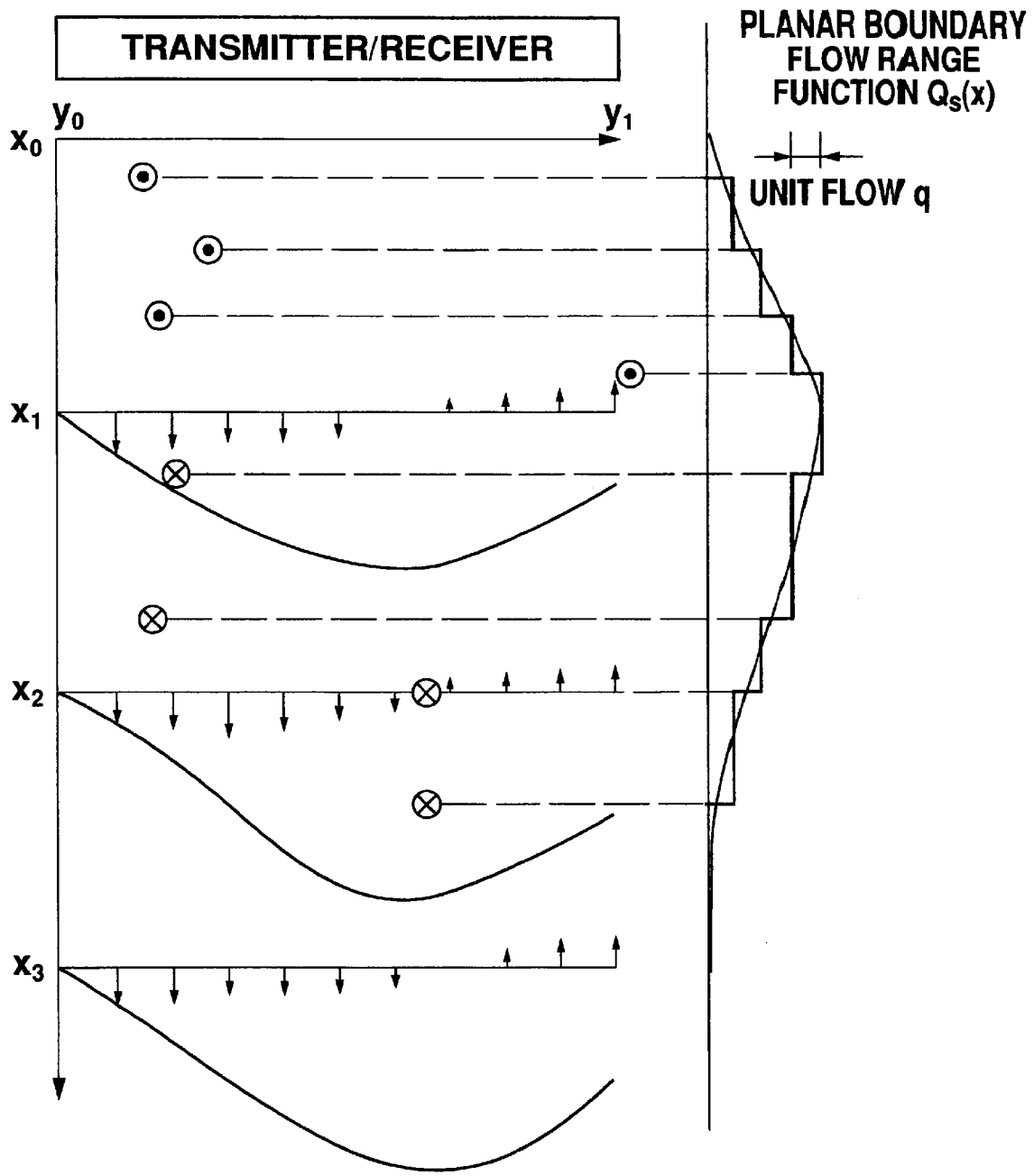
FIG. 18 is a schematic diagram showing the quantization of the planar boundary flow range function and estimation of point sources (simple sources).

FIG. 18 shows a procedure for estimating the distribution of sources/sinks in the observation plane from the planar boundary flow range function $Q_s(x)$. In this procedure, the aforesaid planar boundary flow range function $Q_s(x)$ is first quantized by a unit flow rate q. This unit flow rate q is a streamline interval when a planar flow in the observation plane is displayed. By quantizing in terms of the unit flow rate q, the distribution of sources and sinks corresponding to the streamline interval can be found.

The step graph on the right side of FIG. 18 shows the state where the planar boundary flow range function is quantized (quantized planar boundary flow range function). The positions of the source points or sink points are fixed at locations where the rate of Doppler velocity change in the beam direction is large, as shown by FIG. 13 to FIG. 15 used in describing the principle of the invention. As a result, it is estimated that there are four source points (streamline starting points) and four sink points (streamline end points) in the observation plane as shown in FIG. 18.

Figure 19:
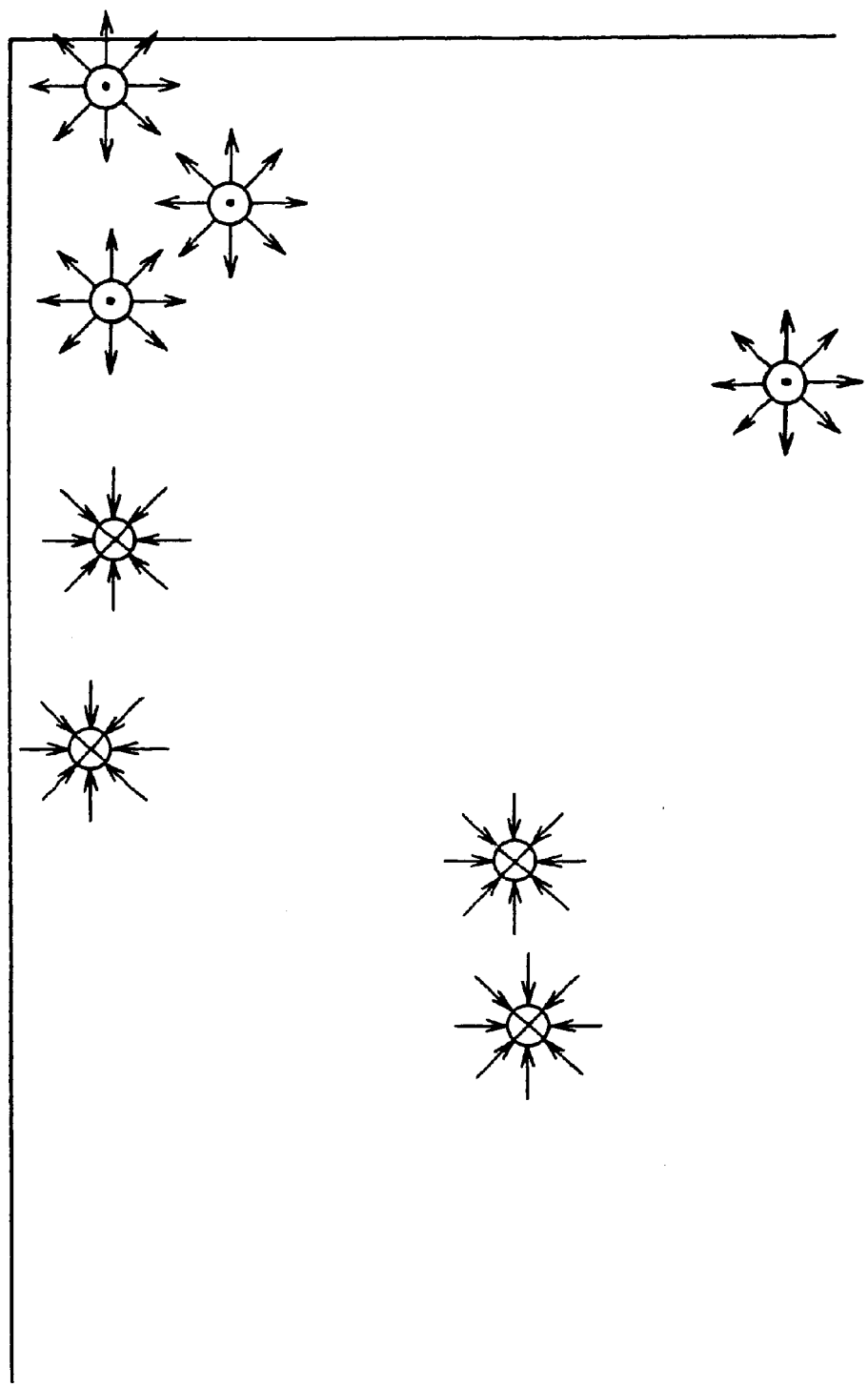
FIG. 19 is a figure showing an example of a point source (simple source) distribution.

FIG. 19 shows the flow velocity distribution due to these estimated simple sources, and a simple source flow function due to the three-dimensional inflow/outflow between layers can thus be found.

Figure 20:
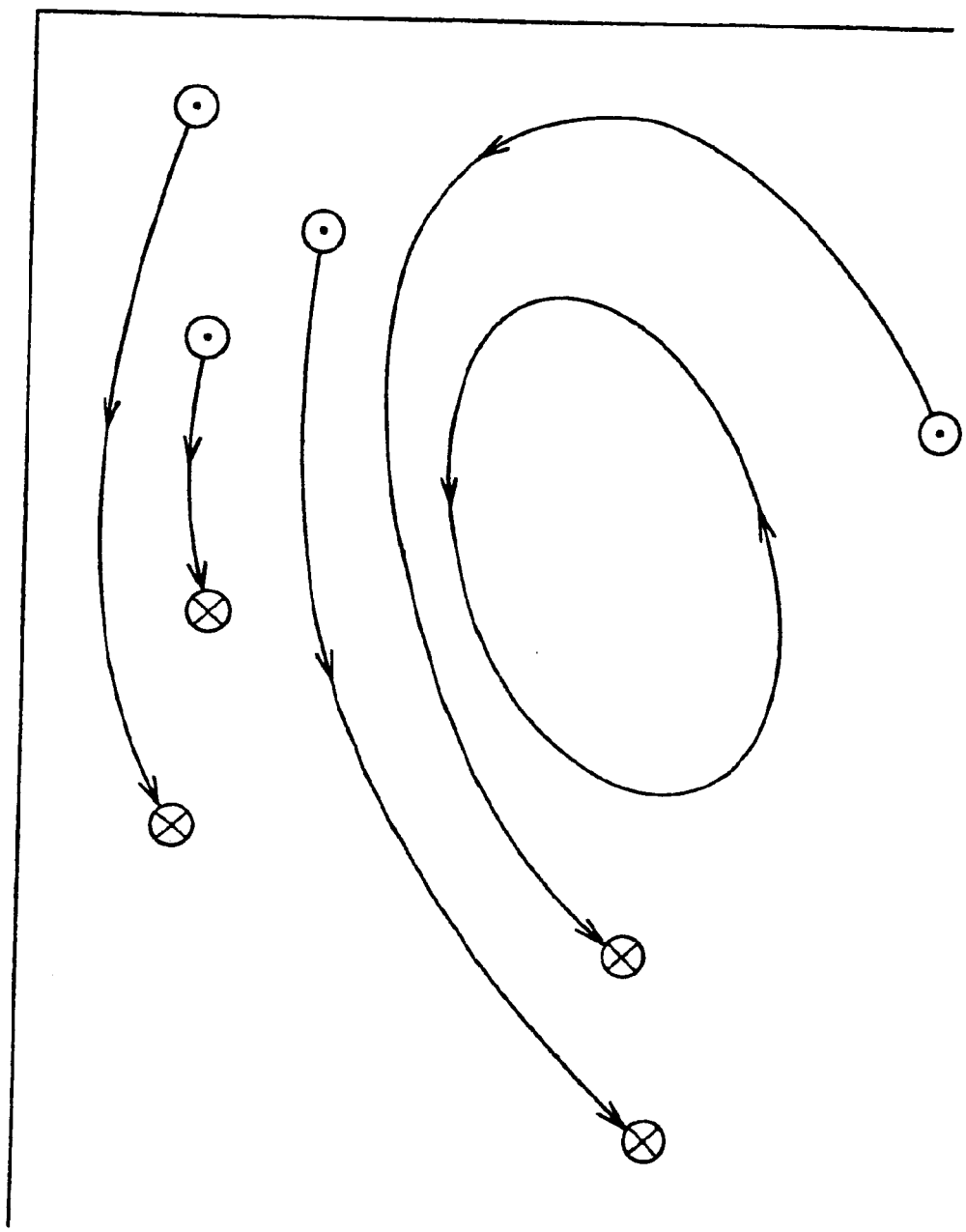
FIG. 20 is a schematic diagram showing an example of a planar streamline found by combining the planar flow function and the simple source flow function.

As is clear from the aforesaid description, by finding the planar flow function based on FIG. 18 and the simple source flow function due to the simple source distribution shown in FIG. 19, the planar flow can be estimated by combining the two. FIG. 20 shows an example of a planar flow resulting from this combination.

The nature of the flow in the observation plane can be understood from the planar streamline shown in FIG. 20. It is for example extremely effective for an overall diagnosis if, in ultrasonic wave diagnosis, this planar streamline display is superposed on the flow display obtained by the conventional Doppler method or a tissue tomogram display obtained by the B mode method.

Process Sequence

Figure 21:
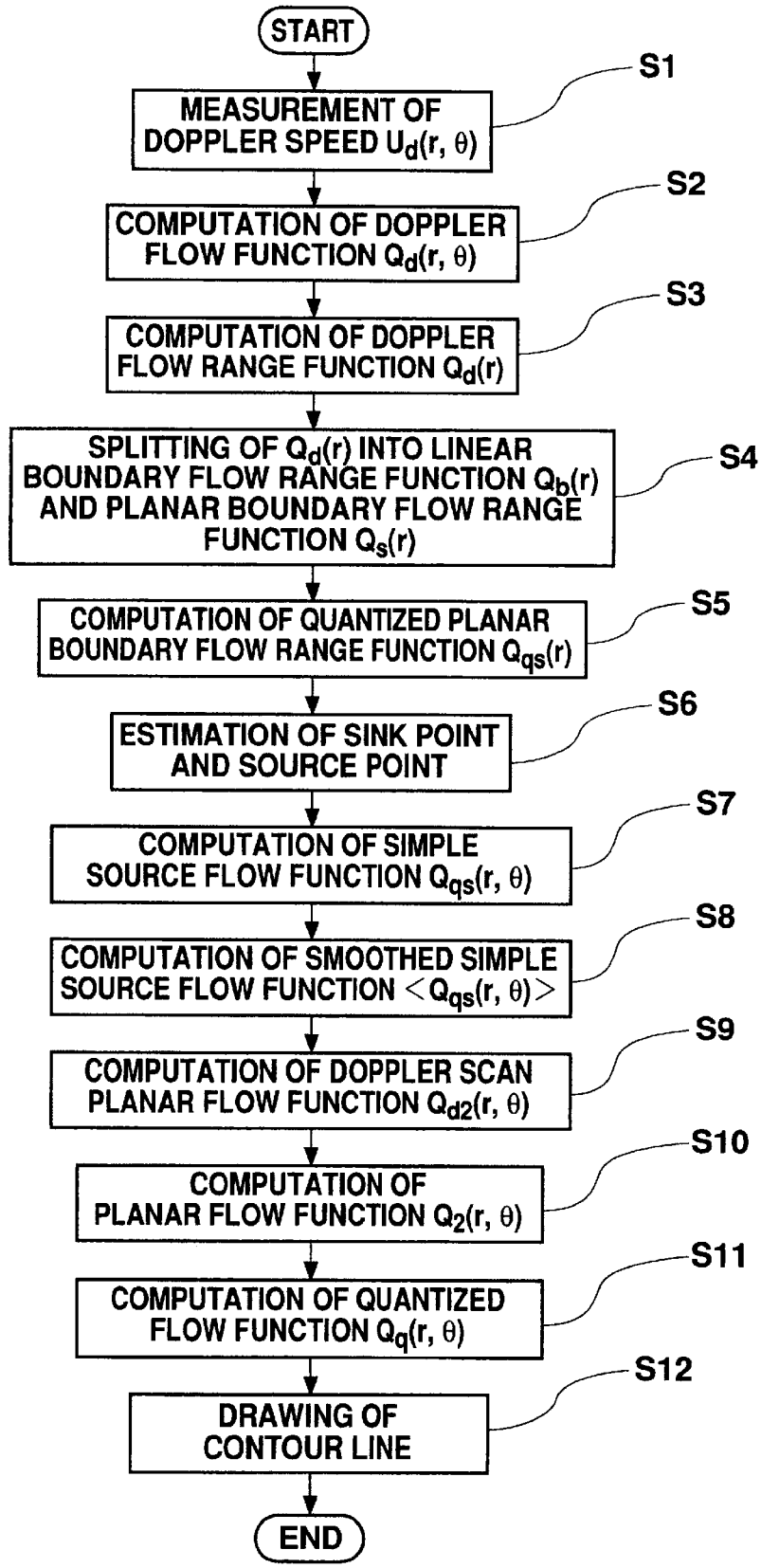
FIG. 21 is a flowchart showing the processing flow according to this embodiment.

Summarizing the processing of the aforementioned embodiment, the flowchart shown in FIG. 21 is obtained. This example shows the case of sector scanning.

First, the distribution of Doppler velocity $u_d(r,\theta)$ in the observation area based on the Doppler method is found by transmitting an observation wave beam (S1).

Next, the Doppler flow function $Q_d(r, \theta)$ is found by integrating this speed $u_d$ for each point $(r,\theta)$ along a path (which is an arc in the case of sector scan) perpendicular to the beam direction (S2).

Based on this distribution, the Doppler flow range function $Q_d(r)$ is then found as a function of the distance r by integrating the Doppler velocity $u_d$ along the arc perpendicular to the beam direction from the side boundary which is the reference line of the observation area to the other side boundary (S3).

Next, the linear boundary flow range function $Q_b(r)$ which shows the two-dimensional flow in the observation area is found from the boundary conditions, and the planar boundary flow range function $Q_s(r)$ which represents three-dimensional inflow/outflow relative to the observation area is found by subtracting $Q_b(r)$ from the Doppler flow range function $Q_d(r)$ (S4). The quantized planar boundary flow range function $Q_{qs}(r)$ is then found by approximating this planar boundary flow range function $Q_s(r)$ by a step function which varies with unit flow rate q (S5). Based on this quantized planar boundary flow range function $Q_{qs}(r)$, a sink position and a source position representing three-dimensional inflow/outflow relative to the observation area are found (S6).

In the step S6, the distance r from the origin of a simple source is estimated based on the position of the steps of $Q_{qs}(r)$. The position of the simple source is then estimated from the point where the rate of change of Doppler velocity on an axis (an arc in the case of sector scan) perpendicular to the beam direction at the distance r is a maximum.

Next, the simple source flow function $Q_{qs}$ which represents a flow rate due to the simple source is found from the distribution of simple sources (S7). The value of the simple source flow function at each point is found by adding the flow rate contribution from each simple source relative to the point.

Next, the smoothed simple source flow function $<Q_{qs}(r, \theta)>$ is found by smoothing the simple source flow function $Q_{qs}(r,\theta)$ is found (S8).

Next, the Doppler scan planar flow function $Q_{d2}(r,\theta)$ is found by subtracting the smoothed simple source flow function $<Q_{qs}(r, \theta)>$ from the Doppler flow function $Q_d(r,\theta)$ (S9). The planar flow amount function $Q_2(r,\theta)$ at each point taking the starting point as a reference is found by adding the bias C(r) to this Doppler scan planar flow amount function (S10). The quantized flow function $Q_q(r,\theta)$ is found by adding this planar flow amount function $Q_2(r,\theta)$ and simple source flow function $Q_{qs}(r,\theta)$ (S11). Finally, the contour line of this quantized flow function $Q_q(r, \theta)$ is found as a planar streamline in the observation area (S12).

Due to the above process, a streamline which represents the flow in the two-dimensional observation area is found based on the measurement results of the Doppler method.

In the above, S3–S8 (computation of smoothed simple source flow function) were performed after S2 (computation of Doppler flow function), but either of these may be performed first. Further, the above-mentioned procedure was an example where the observation wave beam was used to perform sector scanning, but a streamline in the observation area may also be found by an identical procedure in the case of linear scanning.

In the above procedure, S2–S12 may be performed by having a digital computer execute a program comprising the contents of each step.

As described above, according to this invention, the two-dimensional flow and an inter-layer flow relating to inflow/outflow to and from the observation plane are found separately from the Doppler velocity distribution of the reflected wave in the observation plane and then combined, so the planar flow may be precisely estimated.

According to this invention, by separately estimating the two-dimensional flow and three-dimensional inter-layer inflow/outflow from the Doppler velocity distribution using ultrasonic waves or electromagnetic waves, the planar flow in the observation area may be precisely estimated.

As the invention makes it easy to observe and estimate blood flow in the heart, or the movement of ocean currents and clouds, it provides a planar flow estimation method having many different applications in a wide range of fields.

Further, this planar flow is shown as a flow function as mentioned hereabove, and by superposing it on a two-dimensional Doppler image, it provides a display with a very high level of recognition.

What is claimed is:

1. A method comprising:
   a step for scanning an observation wave beam to a predetermined observation plane in a fluid, and measuring the Doppler velocity distribution from the Doppler frequency of the wave reflected from the observation plane,
   a step for performing a linear integration of Doppler velocity along orthogonal paths at right angles to the beam direction in order to calculate a Doppler flow function at points on said orthogonal paths in said observation plane,
   a step for calculating flow rates passing respectively through said orthogonal paths based on said Doppler velocity distribution, and calculating a Doppler flow range function representing a variation of flow rate along the beam direction, a step for separating said Doppler flow range function into a linear boundary flow range function and a planar boundary flow range function based on boundary conditions, a step for quantizing said planar boundary flow range function taking a predetermined flow rate as a unit for quantization in order to calculate a quantized planar boundary flow range function which varies in a stepwise manner, a step for estimating sink points and source points based on a variation rate of Doppler velocity on orthogonal paths corresponding to each step position in said quantized planar boundary flow range function, a step for calculating a simple source flow function representing a flow rate at each point in the observation plane due to an effect of said sink points and source points, from the distribution of said estimated sink points and source points, a step for calculating a smoothed simple source flow function from said simple source flow function, a step for subtracting said smoothed simple source flow function from said Doppler flow function in order to calculate a Doppler scan planar flow function, a step for adjusting said Doppler scan planar flow function based on boundary conditions in order to calculate a planar flow function, a step for calculating a quantized flow function by combining said planar flow function with said simple source flow function, and a step for calculating a contour line of said quantized flow function.

2. A method as defined in claim 1, wherein said source point is taken as a starting point of said contour line, and said sink point is taken as a finishing point of said contour line.

3. A method as defined in claim 1, wherein said observation wave beam is an ultrasonic wave.

4. A method as defined in claim 1, further comprising a step of displaying wherein the contour line of said quantized flow function displayed on another tomogram obtained by scanning with said observation wave beam.

5. A method as defined in claim 1, wherein said step for calculating said planar flow function comprises a step for compensating a quantization error contained in said Doppler scan planar flow function.

6. A method as defined in claim 1, wherein a calculation in said step for calculating said simple source flow function is performed along the same path as the integration path for calculating said Doppler flow function.

7. A computer-readable medium having stored thereon instructions which cause a computer system to perform the steps of:

reading data of a Doppler velocity distribution of an observation plane, performing a linear integration of Doppler velocity along orthogonal paths at right angles to the beam direction in order to calculate a Doppler flow function at points on said orthogonal paths in said observation plane, calculating flow rates passing respectively through said orthogonal paths based on said Doppler velocity distribution, and calculating a Doppler flow range function representing a variation of flow rate along the beam direction, separating said Doppler flow range function into a linear boundary flow range function and a planar boundary flow range function based on boundary conditions, quantizing said planar boundary flow range function taking a predetermined flow rate as a unit for quantization in order to calculate a quantized planar boundary flow range function which varies in a stepwise manner, estimating sink points and source points based on a variation rate of Doppler velocity on orthogonal paths corresponding to each step position in said quantized planar boundary flow range function, calculating a simple source flow function representing a flow rate at each point in the observation plane due to an effect of said sink points and source points, from the distribution of said estimated sink points and source points, calculating a smoothed simple source flow function from said simple source flow function, subtracting said smoothed simple source flow function from said Doppler flow function calculate a Doppler scan planar flow function, adjusting said Doppler scan planar flow function based on boundary conditions in order to calculate a planar flow function, calculating a quantized flow function by combining said planar flow function with said simple source flow function, and calculating a contour line of said quantized flow function.

* * * * *